(12) United States Patent  
Pecinovsky et al.

(10) Patent No.: US 12,228,840 B2  
(45) Date of Patent: *Feb. 18, 2025

(54) NONLINEAR OPTICAL CHROMOPHORES HAVING A DIAMONDOID GROUP ATTACHED THERETO, METHODS OF PREPARING THE SAME, AND USES THEREOF

(71) Applicant: Lightwave Logic, Inc., Englewood, CO (US)

(72) Inventors: Cory Pecinovsky, Lafayette, CO (US); Barry Johnson, Castle Rock, CO (US); Ginelle Ramann, Centennial, CO (US)

(73) Assignee: Lightwave Logic, Inc., Englewood, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,217

(22) Filed: Oct. 10, 2023

(65) Prior Publication Data

US 2024/0045307 A1 Feb. 8, 2024

Related U.S. Application Data

(63) Continuation of application No. 17/358,960, filed on Jun. 25, 2021, now Pat. No. 11,921,401.

(Continued)

(51) Int. Cl.
*G02F 1/00* (2006.01)
*C07D 487/00* (2006.01)
*G02F 1/361* (2006.01)

(52) U.S. Cl.
CPC ......... *G02F 1/3617* (2013.01); *C07D 487/00* (2013.01); *G02F 1/0018* (2013.01); *G02F 1/3612* (2013.01)

(58) Field of Classification Search
CPC .... G02F 1/0018; G02F 1/3612; G02F 1/3617; C07D 487/00

See application file for complete search history.

(56) References Cited

U.S. PATENT DOCUMENTS

| 4,767,169 A | 8/1988 | Teng et al. |
| 4,795,664 A | 1/1989 | Demartino |

(Continued)

FOREIGN PATENT DOCUMENTS

| CN | 103270135 A | 8/2013 | |
| CN | 103923481 A * | 7/2014 | ............. C09B 57/00 |

(Continued)

OTHER PUBLICATIONS

David Briers, Guy Koeckelberghs, Isabel Picard, Thierry Verbiest, Andre' Persoons, Celest Samyn, Novel Chromophore-Functionalized Poly[2-(trifluoromethyl) adamantyl acrylate-methyl vinyl urethane]s with High Poling Stabilities of the Nonlinear Optical Effect, Macromol. Rapid Commun. 2003, 24, 841-846, (2003).*

(Continued)

*Primary Examiner* — Bijan Ahvazi
(74) *Attorney, Agent, or Firm* — Flaster Greenberg P.C.

(57) ABSTRACT

Nonlinear optical chromophores having one or more diamondoid groups covalently attached to the chromophore, methods of making nonlinear optical chromophores, their use in thin films and electro-optical devices containing such nonlinear optical chromophores and thin films comprising the same.

5 Claims, 2 Drawing Sheets

Related U.S. Application Data

(60) Provisional application No. 63/044,057, filed on Jun. 25, 2020.

(56) References Cited

U.S. PATENT DOCUMENTS

| | | | |
|---|---|---|---|
| 4,810,338 | A | 3/1989 | Demartino et al. |
| 4,936,645 | A | 6/1990 | Yoon et al. |
| 5,006,285 | A | 4/1991 | Thackara et al. |
| 5,044,725 | A | 9/1991 | Demartino et al. |
| 5,106,211 | A | 4/1992 | Chiang et al. |
| 5,133,037 | A | 7/1992 | Yoon et al. |
| 5,170,461 | A | 12/1992 | Yoon et al. |
| 5,187,234 | A | 2/1993 | Leslie et al. |
| 5,196,509 | A | 3/1993 | Allen |
| 5,247,042 | A | 9/1993 | Allen et al. |
| 5,326,661 | A | 7/1994 | Sansone et al. |
| 5,384,378 | A | 1/1995 | Etzbach et al. |
| 5,670,091 | A | 9/1997 | Marder et al. |
| 5,679,763 | A | 10/1997 | Jen et al. |
| 6,090,332 | A | 7/2000 | Marder et al. |
| 6,393,190 | B1 | 5/2002 | He et al. |
| 6,444,830 | B1 | 9/2002 | He et al. |
| 6,448,416 | B1 | 9/2002 | He et al. |
| 6,514,434 | B1 | 2/2003 | He et al. |
| 6,584,266 | B1 | 6/2003 | He et al. |
| 6,716,995 | B2 | 4/2004 | Huang et al. |
| 7,425,643 | B1 | 9/2008 | Jen et al. |
| 8,574,467 | B1 * | 11/2013 | Davis ............... C09B 23/0025 528/331 |
| 11,061,297 | B2 | 7/2021 | Yokoyama et al. |
| 11,921,401 | B2 * | 3/2024 | Pecinovsky ........... G02F 1/0018 |
| 2003/0146420 | A1 | 8/2003 | Do et al. |
| 2004/0192940 | A1 * | 9/2004 | Huang ................ C07D 495/04 546/281.1 |
| 2007/0260062 | A1 | 11/2007 | Goetz et al. |
| 2007/0260063 | A1 | 11/2007 | Goetz et al. |
| 2008/0009620 | A1 | 1/2008 | Goetz |
| 2008/0139812 | A1 | 6/2008 | Goetz et al. |
| 2009/0005561 | A1 | 1/2009 | Goetz et al. |
| 2012/0267583 | A1 | 10/2012 | Goetz et al. |
| 2019/0085199 | A1 | 3/2019 | Yokoyama et al. |
| 2020/0093942 | A1 | 3/2020 | Shabat et al. |
| 2020/0388764 | A1 | 12/2020 | Dai et al. |
| 2024/0045306 | A1 * | 2/2024 | Pecinovsky ......... C09B 23/0075 |

FOREIGN PATENT DOCUMENTS

| | | |
|---|---|---|
| CN | 104558004 A | 4/2015 |
| CN | 104974151 A | 10/2015 |
| CN | 107216321 A | 9/2017 |
| CN | 108779197 A | 11/2018 |
| CN | 110156756 A | 8/2019 |
| EP | 0590421 A1 | 4/1994 |
| EP | 3431515 A1 | 1/2019 |
| JP | H01124834 A | 5/1989 |
| JP | H0561082 A | 3/1993 |
| JP | 2002363551 A | 12/2002 |
| JP | 2002371271 A | 12/2002 |
| WO | 0009613 A2 | 2/2000 |
| WO | 2001079750 A1 | 10/2001 |
| WO | 2018216013 A1 | 11/2018 |
| WO | 2020118116 A1 | 6/2020 |

OTHER PUBLICATIONS

Briers, et al., "Novel Chromophore-Functionalized Poly[2-(trifluoromethyl) adamantyl acrylate-methyl vinyl urethane]s with High Poling Stabilities of the Nonlinear Optical Effect", David, Guy Koeckelberghs, Isabel Picard, Thierry Verbiest, Andre' Persoons, Celest Samyn,, Macromol. Rapid Commun. 2003, 24,, 2003, 841-846.

Gund, Tamara M, et al., "Diamantane. I.1 Preparation of Diamantane. Physical and Spectral Properties", J. Org. Chem. 39 (20): 2979-2987,, Oct. 1, 1974, 2979-2987 pages.

Teng, Cahia-Chi, "Measuring Electro-Optic Constants of a Poled Film", in Nonlinear Optics of Organic Molecules and Polymers, Chp. 7, 447-49 (Hari Singh Nalwa & Seizo Miyata eds, 1997.

Thiel, C. W., et al., "Four-Wave Mixing and its Applications", www.physics.montana.edu.students.thiel.docs/FWMixing.pdf;, 2008, 20 pages.

Wei, Li, "Adamantane-Substituted Acridine Donor for Blue Dual Fluorescence and Efficient Organic Light-Emitting Diodes", Angewandte Chemie International Edition, vol. 58, No. 2, Jan. 8, 2019, pp. 582-586.

Alex K.-Y. Jen, et al., "Highly efficient and thermally stable organic/polymeric electro-optic materials by dendritic approach", Proceedings of SPIE, vol. 4461, Dec. 31, 2001, pp. 172-179.

Su Huang, et al., "Enhanced temporal stability of a highly efficient guest-host electro-optic polymer through a barrier layer assisted poling process", Journal of Materials Chemistry, vol. 22, No. 38, Aug. 9, 2012, pp. 20353-20357.

Haoran Wang, et al., "A study of two thermostable NLO chromophores with different TT-electron bridges using fluorene as the donor", New Journal of Chemistry, vol. 39, No. 2, Nov. 13, 2014, pp. 1038-1044.

Simon Pascal, et al., "Design of Near-Infrared-Absorbing Unsymmetrical Polymethine Dyes with Large Quadratic Hyperpolarizabilities", Chemistry of Materials, vol. 30, No. 10, Apr. 18, 2018, pp. 3410-3418.

Huang, et al., "Highly efficient electro-optic polymers through improved poling using a thin TiO2-modified transparent electrode", Applied Physics Letters, vol. 96, Issue 24, Jun. 2010, 3 pages.

* cited by examiner

NONLINEAR OPTICAL CHROMOPHORES HAVING A DIAMONDOID GROUP ATTACHED THERETO, METHODS OF PREPARING THE SAME, AND USES THEREOF

CROSS-REFERENCE TO RELATED APPLICATIONS

This application is a continuation of U.S. Non-Provisional application Ser. No. 17/358,960, filed Jun. 25, 2021, which claims the benefit of U.S. Provisional Patent Application No. 63/044,057, filed Jun. 25, 2020, the entire contents of which are hereby incorporated herein by reference.

BACKGROUND OF THE INVENTION

Nonlinear optical (NLO) chromophores provide the electro-optic (EO) activity in poled, electro-optic polymer devices. Electro-optic polymers have been investigated for many years as an alternative to inorganic materials such as lithium niobate in electro-optic devices. Electro-optic devices may include, for example, external modulators for telecom, RF photonics, and optical interconnects and so forth. Polymeric electro-optic materials have demonstrated enormous potential for core application in a broad range of next-generation systems and devices, including phased array radar, satellite and fiber telecommunications, cable television (CATV), optical gyroscopes for application in aerial and missile guidance, electronic counter measure (ECM) systems, backplane interconnects for high-speed computation, ultraquick analog-to-digital conversion, land mine detection, radio frequency photonics, spatial light modulation and all-optical (light-switching-light) signal processing.

Many NLO molecules (chromophores) have been synthesized that exhibit high molecular electro-optic properties. The product of the molecular dipole moment ($\mu$) and hyperpolarizability ($\beta$) is often used as a measure of molecular electro-optic performance due to the dipole's involvement in material processing. See Dalton et al., "New Class of High Hyperpolarizability Organic Chromophores and Process for Synthesizing the Same", WO 00/09613.

Nevertheless extreme difficulties have been encountered translating microscopic molecular hyperpolarizabilities ($\beta$) into macroscopic material hyperpolarizabilities ($\chi^2$). Molecular subcomponents (chromophores) must be integrated into NLO materials that exhibit (i) a high degree of macroscopic nonlinearity and (ii) sufficient temporal, thermal, chemical and photochemical stability. High electro-optic activity and the stability of electro-optic activity, which is also referred to as "temporal stability," are important for commercially viable devices. Electro-optic activity may be increased in electro-optic polymers by increasing the concentration of nonlinear optical chromophores in a host polymer and by increasing of the electro-optic property of chromophores. However, some techniques for increasing chromophore concentration may decrease temporal stability. Simultaneous solution of these dual issues is regarded as the final impediment in the broad commercialization of EO polymers in numerous devices and systems.

The production of high material hyperpolarizabilities ($\chi^2$) is limited by the poor social character of NLO chromophores. Commercially viable materials must incorporate chromophores at large molecular densities with the requisite molecular moment statistically oriented along a single material axis. In order achieve such an organization, the charge transfer (dipole) character of NLO chromophores is commonly exploited through the application of an external electric field during material processing that creates a localized lower-energy condition favoring noncentrosymmetric order. Unfortunately, at even moderate chromophore densities, molecules form multi-molecular dipolarly-bound (centrosymmetric) aggregates that cannot be dismantled via realistic field energies. To overcome this difficulty, integration of anti-social dipolar chromophores into a cooperative material architecture is commonly achieved through the construction of physical barriers that limit proximal intermolecular relations.

Nevertheless, the most daunting problem in the production of commercially successful NLO polymers is the issue of resultant long-term material stability. This is likely due to the reinstitution of centrosymmetry as a result of molecular mobility over time. The effectiveness of organic NLO materials having high hyperpolarizabilities is limited by the tendency of these materials to aggregate when processed as well as the thermal stability of those resultant materials. Accordingly, there exists a need for improved nonlinear optically active materials having large hyperpolarizabilities and that when employed in electro-optic devices, exhibit large electro-optic coefficients and high thermal stability.

BRIEF SUMMARY OF THE INVENTION

The present invention is directed, in general, nonlinear optical chromophores, methods of making nonlinear optical chromophores, their use in thin films and electro-optical devices containing such nonlinear optical chromophores and thin films comprising the same. Various embodiments of the present invention thus provide nonlinear optical chromophores having one or more diamondoid groups covalently attached to the chromophore. Various embodiments of the present invention provide nonlinear optical chromophores having one or more diamondoid groups covalently attached to the chromophore which exhibit high molecular electro-optic properties and excellent stability. Various embodiments of the present invention provide nonlinear optical chromophores having one or more diamondoid groups covalently attached to the chromophore, which chromophores can exhibit long term stability in their macroscopic electro-optic properties when dispersed in a host polymer matrix and poled, with aggregation of chromophore molecules minimized. Various embodiments of the present invention provide nonlinear optical chromophores having one or more diamondoid groups covalently attached to the chromophore, which chromophores can exhibit improved poling efficiency when dispersed in a host polymer matrix and poled. Various embodiments of the present invention provide nonlinear optical chromophores having one or more diamondoid groups covalently attached to the chromophore, which chromophores can exhibit increased loading when dispersed in a host polymer matrix.

Various embodiments of the present invention include nonlinear optical chromophores of the general formula (I):

$$D\text{-}\Pi\text{-}A \qquad (I)$$

wherein D represents an organic electron-donating group; A represents an organic electron-accepting group having an electron affinity greater than the electron affinity of D; and Π represents a Π-bridge between A and D; wherein at least one diamondoid is covalently attached to the nonlinear optical chromophore.

Various other embodiments of the present invention include electro-optical thin films comprising a nonlinear optical chromophore according to any of the foregoing embodiments dispersed and poled within a host polymer matrix. Still other various embodiments of the present invention include electro-optic devices comprising electro-optical thin films according to any of the foregoing embodiments. Various other embodiments of the present invention include methods which comprise: synthesizing a nonlinear optical chromophore of the general formula (I):

$$D\text{-}\Pi\text{-}A \tag{I}$$

wherein D represents an organic electron-donating group; A represents an organic electron-accepting group having an electron affinity greater than the electron affinity of D; and Π represents a Π-bridge between A and D; and covalently attaching at least one diamondoid group to the nonlinear optical chromophore during the synthesis.

In various embodiments of the present invention, nonlinear optical chromophores of the general formula (I) have up to five diamondoid groups covalently attached to the structure. In various preferred embodiments of the present invention, nonlinear optical chromophores of the general formula (I) have one, two or three diamondoid groups covalently attached to the structure. In various preferred embodiments of the present invention, nonlinear optical chromophores of the general formula (I) have one, two or three diamondoid groups covalently attached to the structure, which may all be bound to the Π-bridge. In various preferred embodiments of the present invention, nonlinear optical chromophores of the general formula (I) have one, two or three diamondoid groups covalently attached to the structure, which may be bound to D, A or the Π-bridge. In various preferred embodiments of the present invention, one or more diamondoid groups is covalently attached to D or the Π-bridge.

In various preferred embodiments of the present invention, the at least one diamondoid comprises an adamantyl group. In various preferred embodiments of the present invention, the at least one diamondoid comprises a diamantyl group. In various preferred embodiments of the present invention wherein a nonlinear optical chromophores of the general formula (I) has up to five diamondoid groups covalently attached to the structure, and in various preferred embodiments of the present invention all of the diamondoids can be the same.

Other aspects, features and advantages will be apparent from the following disclosure, including the detailed description, preferred embodiments, and the appended claims.

BRIEF DESCRIPTION OF SEVERAL VIEWS OF THE DRAWINGS

The foregoing summary, as well as the following detailed description of preferred embodiments of the invention, will be better understood when read in conjunction with the appended drawings. For purposes of illustration the invention, there are shown in the drawings embodiments which are presently preferred. It should be understood, however, that the invention is not limited to the precise arrangements and instrumentalities shown.

In the Drawings.

DETAILED DESCRIPTION OF THE INVENTION

Figure 1:
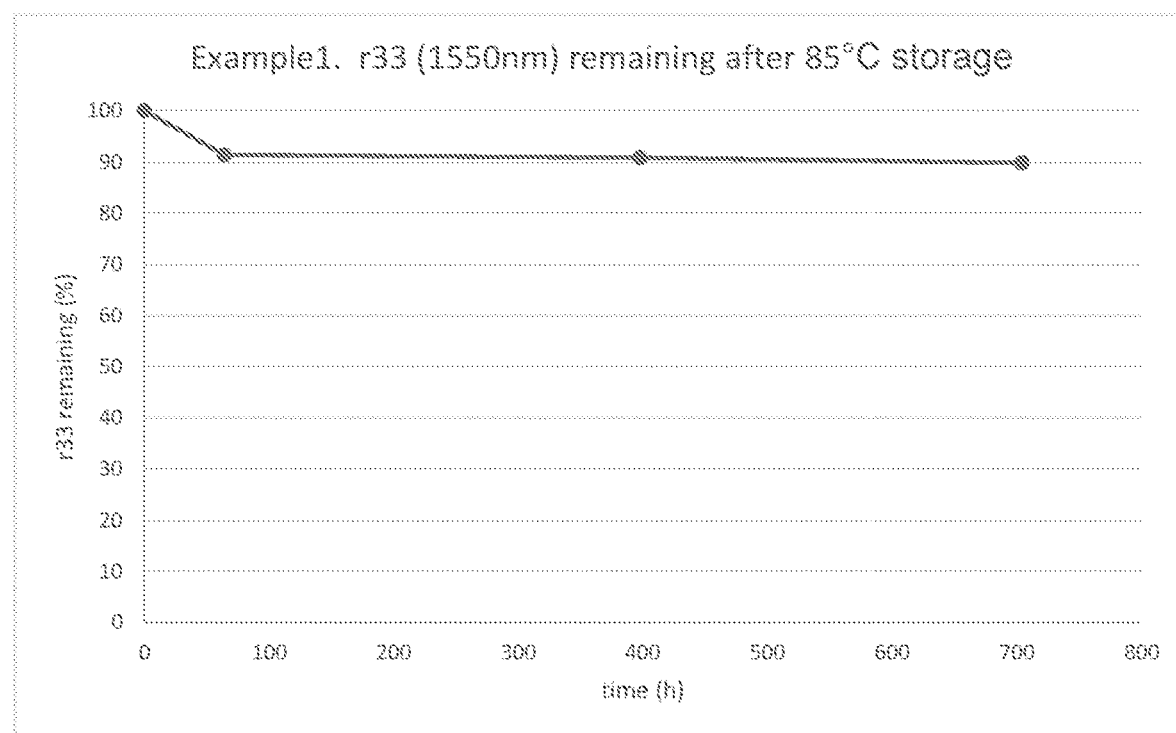
FIG. 1 is a graphical depiction of the temporal thermal stability of a thin film coating prepared using the chromophore of Synthesis Example 1.

As used herein, the singular terms "a" and "the" are synonymous and used interchangeably with "one or more" and "at least one," unless the language and/or context clearly indicates otherwise. Accordingly, for example, reference to "a polymer" or "the polymer" herein or in the appended claims can refer to a single polymer or more than one polymer. As a further example, and not limited to only electron-donating groups, reference to "an electron-donating group" or "the electron-donating group" herein or in the appended claims can refer to a single electron-donating group or more than on electron-donating group (e.g., "D" in any molecular formula herein may represent two or more electron-donating groups both bound to the Π-bridge). Additionally, all numerical values, unless otherwise specifically noted, are understood to be modified by the word "about."

As used herein, the term "nonlinear optic chromophore" (NLOC) refers to molecules or portions of a molecule that create a nonlinear optic effect when irradiated with light. The chromophores are any molecular unit whose interaction with light gives rise to the nonlinear optical effect. The desired effect may occur at resonant or nonresonant wavelengths. The activity of a specific chromophore in a nonlinear optic material is stated as its hyper-polarizability, which is directly related to the molecular dipole moment of the chromophore. The various embodiments of NLO chromophores of the present invention are useful structures for the production of NLO effects.

The first-order hyperpolarizability ($\beta$) is one of the most common and useful NLO properties. Higher-order hyperpolarizabilities are useful in other applications such as all-optical (light-switching-light) applications. To determine if a material, such as a compound or polymer, includes a nonlinear optic chromophore with first-order hyperpolar character and a sufficient electro-optic coefficient ($r_{33}$), which is a function of $\beta$, the following test may be performed. First, the material in the form of a thin film is placed in an electric field to align the dipoles. This may be performed by sandwiching a film of the material between electrodes, such as indium tin oxide (ITO) substrates, gold films, or silver films, for example.

To generate a poling electric field, an electric potential is then applied to the electrodes while the material is heated to near its glass transition ($T_g$) temperature. After a suitable period of time, the temperature is gradually lowered while maintaining the poling electric field. Alternatively, the material can be poled by corona poling method, where an electrically charged needle at a suitable distance from the material film provides the poling electric field. In either instance, the dipoles in the material tend to align with the field.

The nonlinear optical property of the poled material is then tested as follows. Polarized light, often from a laser, is passed through the poled material, then through a polarizing filter, and to a light intensity detector. If the intensity of light received at the detector changes as the electric potential applied to the electrodes is varied, the material incorporates a nonlinear optic chromophore and has an electro-optically variable refractive index. A more detailed discussion of techniques to measure the electro-optic constants of a poled film that incorporates nonlinear optic chromophores may be found in Chia-Chi Teng, Measuring Electro-Optic Constants of a Poled Film, in Nonlinear Optics of Organic Molecules and Polymers, Chp. 7, 447-49 (Hari Singh Nalwa & Seizo Miyata eds., 1997), incorporated by reference in its entirety, except that in the event of any inconsistent disclosure or definition from the present application, the disclosure or definition herein shall be deemed to prevail.

The relationship between the change in applied electric potential versus the change in the refractive index of the material may be represented as its EO coefficient $r_{33}$. This effect is commonly referred to as an electro-optic, or EO, effect. Devices that include materials that change their refractive index in response to changes in an applied electric potential are called electro-optical (EO) devices.

The second-order hyperpolarizability ($\gamma$) or third-order susceptibility ($\chi^{(3)}$) are the normal measures of third-order NLO activity. While there are several methods used to measure these properties, degenerate four-wave mixing (DFWM) is very common. See C. W. Thiel, "For-wave Mixing and Its Applications," http://www.physics.montana.edu.students.thiel.docs/FWMixing.pdf, the entire contents of which are hereby incorporated herein by reference. Referring to Published U.S. patent application No. US 2012/0267583A1, the entire contents of which are incorporated herein by reference, a method of evaluating third-order NLO properties of thin films, known in the art as Degenerate Four Wave Mixing (DFWM), can be used. In FIG. 4 of US 2012/0267583A1, Beams 1 and 2 are picosecond, coherent pulses, absorbed by the NLO film deposited on a glass substrate. Beam 3 is a weaker, slightly delayed beam at the same wavelength as Beams 1 and 2. Beam 4 is the resulting product of the wave mixing, diffracted off of the transient holographic grating, produced by interferences of beams 1 and 2 in the NLO material of the film. Beam 3 can be a "control" beam at a telecom wavelength which produces a "signal" beam at a frequency not absorbed by the NLO material.

Nonlinear optical chromophores in accordance with the various embodiments of the invention have the general formula (I):

wherein D represents an organic electron-donating group; A represents an organic electron-accepting group having an electron affinity greater than the electron affinity of D; and Π represents a Π-bridge between A and D. The terms electron-donating group (donor or "D"), Π-bridge (bridging group or "Π"), and electron-accepting group (acceptor or "A"), and general synthetic methods for forming D-Π-A chromophores are known in the art, for example as described in U.S. Pat. Nos. 5,670,091, 5,679,763, 6,090,332, and 6,716,995, the entire contents of each of which is incorporated herein by reference.

An acceptor is an atom or group of atoms that has a low reduction potential, wherein the atom or group of atoms can accept electrons from a donor through a Π-bridge. The acceptor (A) has a higher electron affinity that does the donor (D), so that, at least in the absence of an external electric field, the chromophore is generally polarized in the ground state, with relatively more electron density on the acceptor (D). Typically, an acceptor group contains at least one electronegative heteroatom that is part of a pi bond (a double or triple bond) such that a resonance structure can be drawn that moves the electron pair of the pi bond to the heteroatom and concomitantly decreases the multiplicity of the pi bond (i.e., a double bond is formally converted to single bond or a triple bond is formally converted to a double bond) so that the heteroatom gains formal negative charge. The heteroatom may be part of a heterocyclic ring. Exemplary acceptor groups include but are not limited to —$NO_2$, —CN, —CHO, COR, $CO_2R$, —$PO(OR)_3$, —SOR, —$SO_2R$, and —$SO_3R$ where R is alkyl, aryl, or heteroaryl. The total number of heteroatoms and carbons in an acceptor group is about 30, and the acceptor group may be substituted further with alkyl, aryl, and/or heteroaryl.

Suitable electron-accepting groups "A" (also referred to in the literature as electron-withdrawing groups) for nonlinear optical chromophores in accordance with the various embodiments of the present invention include those described in published U.S. patent applications: US 2007/0260062; US 2007/0260063; US 2008/0009620; US 2008/0139812; US 2009/0005561; US 2012/0267583A1 (collectively referred to as "the prior publications"), each of which is incorporated herein by reference in its entirety; and in U.S. Pat. Nos. 6,584,266; 6,393,190; 6,448,416; 6,44,830; 6,514,434; 5,044,725; 4,795,664; 5,247,042; 5,196,509; 4,810,338; 4,936,645; 4,767,169; 5,326,661; 5,187,234; 5,170,461; 5,133,037; 5,106,211; and 5,006,285; each of which is also incorporated herein by reference in its entirety.

In various nonlinear optical chromophores in accordance with various preferred embodiments of the present invention, suitable electron-accepting groups include those according to general formula ($I^a$):

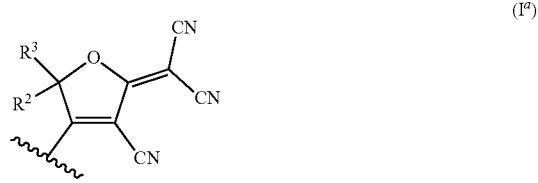

wherein $R^2$ and $R^3$ each independently represents a moiety selected from the group consisting of H, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, and $(CH_2)_n$—O—$(CH_2)_n$ where n is 1-10.

As used herein, ⤳ represents a point of bonding to another portion of a larger molecular structure. In various preferred embodiments, one or both of $R^2$ and $R^3$ represent a halogen-substituted moiety. Halogen-substituted may refer to mono-, di-, tri- and higher degrees of substitution. In various preferred embodiments, one of $R^2$ and $R^3$ represent a halogen-substituted alkyl moiety and the other represents an aromatic moiety. In various preferred embodiments, one of $R^2$ and $R^3$ represent a halogen-substituted aromatic moiety and the other represents an alkyl moiety. In various preferred embodiments, the electron-accepting group can be

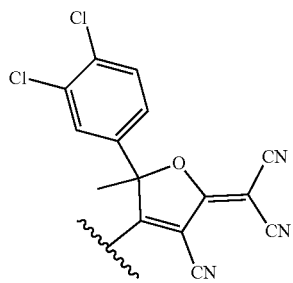 [SMILES: *C1=C(C#N)C(=C(C#N)C#N)OC1(C)c1ccc(Cl)c(Cl)c1]

In various preferred embodiments, the electron-accepting group can be

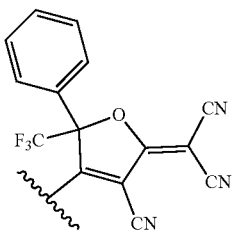 [SMILES: *C1=C(C#N)C(=C(C#N)C#N)OC1(c1ccccc1)C(F)(F)F]

In various preferred embodiments, the electron-accepting group can be

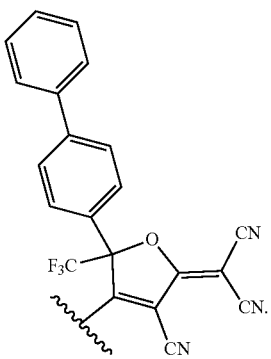 [SMILES: *C1=C(C#N)C(=C(C#N)C#N)OC1(c1ccc(-c2ccccc2)cc1)C(F)(F)F]

A donor includes an atom or group of atoms that has a low oxidation potential, wherein the atom or group of atoms can donate electrons to an acceptor "A" through a Π-bridge. The donor (D) has a lower electron affinity that does the acceptor (A), so that, at least in the absence of an external electric field, the chromophore is generally polarized, with relatively less electron density on the donor (D). Typically, a donor group contains at least one heteroatom that has a lone pair of electrons capable of being in conjugation with the p-orbitals of an atom directly attached to the heteroatom such that a resonance structure can be drawn that moves the lone pair of electrons into a bond with the p-orbital of the atom directly attached to the heteroatom to formally increase the multiplicity of the bond between the heteroatom and the atom directly attached to the heteroatom (i.e., a single bond is formally converted to double bond, or a double bond is formally converted to a triple bond) so that the heteroatom gains formal positive charge. The p-orbitals of the atom directly attached to the heteroatom may be vacant or part of a multiple bond to another atom other than the heteroatom. The heteroatom may be a substituent of an atom that has pi bonds or may be in a heterocyclic ring. Exemplary donor groups include but are not limited to $R_2N$— and, $R_nX^1$—, where R is alkyl, aryl or heteroaryl, $X^1$ is O, S, P, Se, or Te, and n is 1 or 2. The total number of heteroatoms and carbons in a donor group may be about 30, and the donor group may be substituted further with alkyl, aryl, or heteroaryl.

Suitable electron-donating groups "D" for nonlinear optical chromophores in accordance with the various embodiments of the present invention include those described in published U.S. patent applications: US 2007/0260062; US 2007/0260063; US 2008/0009620; US 2008/0139812; US 2009/0005561; US 2012/0267583A1 (collectively referred to as "the prior publications"), each of which is incorporated herein by reference in its entirety; and in U.S. Pat. Nos. 6,584,266; 6,393,190; 6,448,416; 6,44,830; 6,514,434; 5,044,725; 4,795,664; 5,247,042; 5,196,509; 4,810,338; 4,936,645; 4,767,169; 5,326,661; 5,187,234; 5,170,461; 5,133,037; 5,106,211; and 5,006,285; each of which is also incorporated herein by reference in its entirety.

In various preferred embodiments, the electron-donating groups can include quinolinyl groups which may be substituted or unsubstituted, including hydro and alkyl substituents, aryl substituents and combinations thereof. Such quinolinyl groups may have one or more diamondoid groups covalently attached thereto in accordance with various embodiments of the present invention. In various preferred embodiments, the electron-donating groups can include alkoxyphenyl substituted quinolones such as, for example:

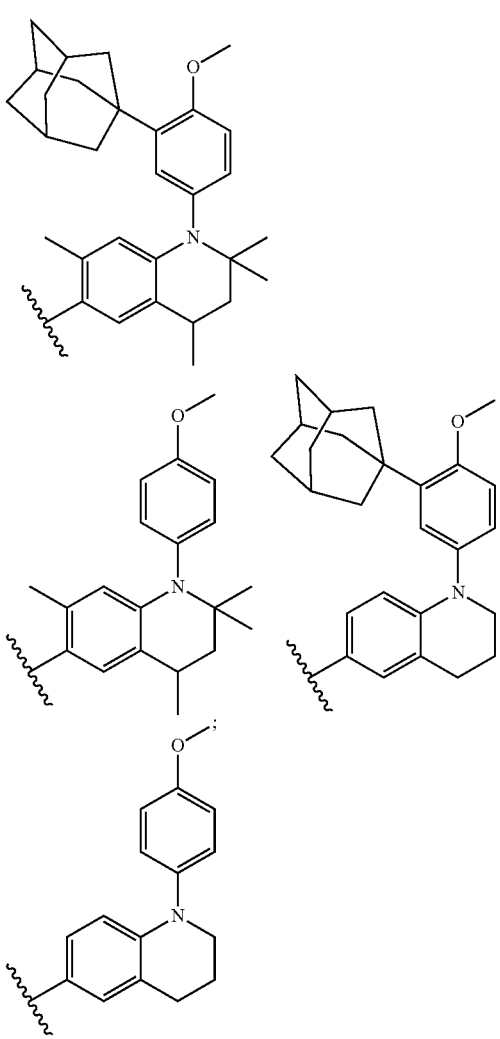

or for example, aromatic nitrogen containing groups such as:

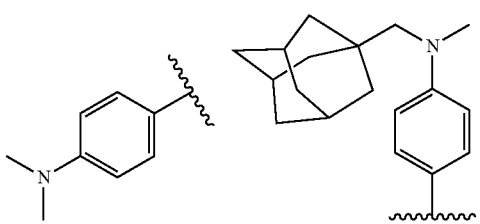

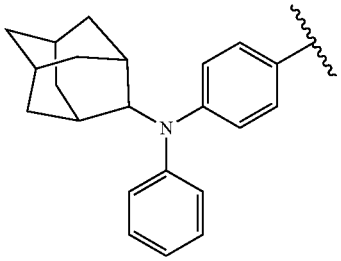

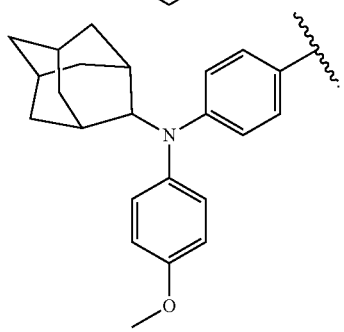

A "Π-bridge" includes an atom or group of atoms through which electrons may be delocalized from an electron donor (defined above) to an electron acceptor (defined above) through the orbitals of atoms in the bridge. Such groups are very well known in the art. Typically, the orbitals will be p-orbitals on double (sp$^2$) or triple (sp) bonded carbon atoms such as those found in alkenes, alkynes, neutral or charged aromatic rings, and neutral or charged heteroaromatic ring systems. Additionally, the orbitals may be p-orbitals on atoms such as boron or nitrogen. Additionally, the orbitals may be p, d or f organometallic orbitals or hybrid organometallic orbitals. The atoms of the bridge that contain the orbitals through which the electrons are delocalized are referred to here as the "critical atoms." The number of critical atoms in a bridge may be a number from 1 to about 30. The critical atoms may be substituted with an organic or inorganic group. The substituent may be selected with a view to improving the solubility of the chromophore in a polymer matrix, to enhancing the stability of the chromophore, or for other purpose.

Suitable bridging groups (II) for nonlinear optical chromophores according to general formula (I) of the present invention include those described in U.S. Pat. Nos. 6,584,266; 6,393,190; 6,448,416; 6,44,830; 6,514,434; each of which is also incorporated herein by reference in its entirety.

In various preferred embodiments, bridging groups (II) for nonlinear optical chromophores according to general formula (I) of the present invention include those of the general formula (II$^a$)

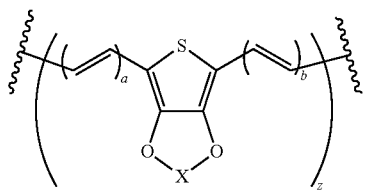

(II$^a$)

wherein X represents a substituted or unsubstituted, branched or unbranched $C_2$-$C_4$ diyl moiety; wherein each a and b independently represents an integer of 0 to 3; and z represents an integer of 1 to 3. In various embodiments wherein a or b in general formula (II$^a$) is 1, that carbon-carbon double bond in the formula can be replaced with a carbon-carbon triple bond. Alternatively, in various preferred embodiments, bridging groups (II) for nonlinear optical chromophores according to general formula (I) of the present invention include those of the general formula (II$^b$)

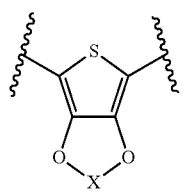

(II$^b$)

wherein X represents a substituted or unsubstituted, branched or unbranched $C_2$-$C_4$ diyl moiety. In various embodiments of the present invention wherein one or more diamondoid groups is covalently attached to a bridging group according to general formulae II$^a$ or II$^b$, the one or more diamondoid groups may be bound, for example, to the sulfur or oxygen atoms of the thiophene group or to one or more carbon atoms in X through an ether or thioether linkage.

In various preferred embodiments, bridging groups (II) for nonlinear optical chromophores according to general formula (I) of the present invention include those of the general formula (II$^c$):

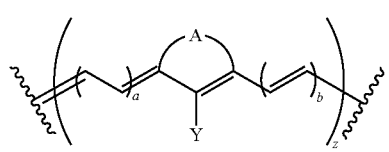

(II$^c$)

wherein each Y independently represents: a diamondoid-containing group covalently bound to the bridging group through any of the various linkages described herein below including but not limited to ether and thioether linkages; or each Y may represent a hydrogen, an alkyl group, aryl group, sulfur or oxygen linked alkyl or aryl group, or a branched or unbranched, optionally heteroatom-containing $C_1$-$C_4$ substituent; wherein each a and b independently represents an integer of 0 to 3; z represents an integer of 1 to 3; and wherein each arc A independently represents a substituted or unsubstituted $C_2$-$C_4$ alkyl group, which together with the carbon bearing the Y substituent and its two adjacent carbon atoms forms a cyclic group. Substituted or unsubstituted $C_2$-$C_4$ alkyl groups which constitute arc A may include 1 to 4 hydrogen substituents each comprising a moiety selected from the group consisting of substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, and $(CH_2)_n$—O—$(CH_2)_n$ where n is 1-10. In various preferred embodiments, z represents 1. In various embodiments according to the present invention, the electron-donating group or electron-accepting group can include one or more covalently bound diamondoid groups, and Y in general formula II$^c$ may represent any of the above substituents. In certain preferred embodiments, a chromophore may include an electron-donating group including one or more covalently linked diamondoid groups, preferably adamantyl, and the bridging group may include an isophorone group in accordance with general formula II$^c$ wherein Y represent an aryl thioether substituent.

In various preferred embodiments, bridging groups (II) for nonlinear optical chromophores according to general formula (I) of the present invention include those of the general formula (II$^d$)

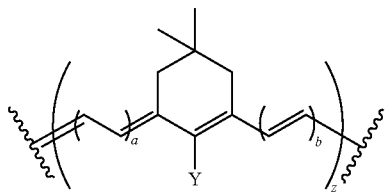

(II$^d$)

wherein each Y independently represents: a diamondoid-containing group covalently bound to the bridging group through any of the various linkages described herein below including but not limited to ether and thioether linkages; or each Y may represent a hydrogen, an alkyl group, aryl group, sulfur or oxygen linked alkyl or aryl group, an aryl group (optionally bearing a diamondoid group) linked directly by a carbon-carbon bond (e.g., adamantly anisole), a halogen, a halogenated alkyl group, a halogenated aryl group, or a branched or unbranched, optionally heteroatom-containing $C_1$-$C_4$ substituent; wherein each a and b independently represents an integer of 0 to 3; and z represents an integer of 1 to 3. In various embodiments according to the present invention, the electron-donating group or electron-accepting group can include one or more covalently bound diamondoid groups, and Y in general formula II$^d$ may represent any of the above substituents. In certain preferred embodiments, a chromophore may include an electron-donating group including one or more covalently linked diamondoid groups, preferably adamantyl, and the bridging group may include an isophorone group in accordance with general formula II$^d$ wherein Y represent an aryl thioether substituent. In various embodiments, each of the geminal methyl groups on the isophorone bridge of the general formula II$^d$ can instead independently represent a moiety selected from the group consisting of substituted or unsubstituted $C_1$-$C_{10}$ alkyl, substituted or unsubstituted $C_2$-$C_{10}$ alkenyl, substituted or unsubstituted $C_2$-$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, halogens, halogenated alkyl groups (e.g., —$CF_3$), halogenated aryls and heteroaryl groups (e.g., pentafluorothiophenol), and $(CH_2)_n$—O—$(CH_2)_n$ where n is 1-10.

For example, bridging groups (II) for nonlinear optical chromophores according to general formula (I) of the present invention can include:

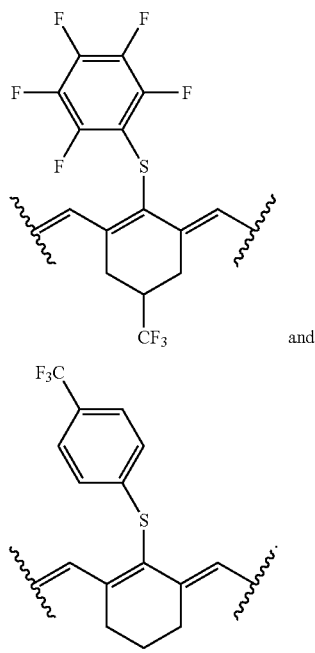

Nonlinear optical chromophores according to the various embodiments of the present invention further include one or more diamondoids covalently attached to the chromophore. The one or more diamondoids may be attached to the electron donating group, electron accepting group and/or Π-bridge, and may be covalently bonded to the various chromophores at the 1-position or 2-position of the diamondoid. The one or more diamondoids generally extend outward from the chromophore and create steric hindrance (i.e., "spacing") between two or more of the chromophore molecules in a material containing the chromophores, and thus serve to prevent aggregation during and after poling.

Diamondoids suitable for use in the various embodiments of the present invention include adamantane ($C_{10}H_{16}$), iceane ($C_{12}H_{18}$), diamantane ($C_{14}H_2O$), triamantane ($C_{18}H_{24}$), isotetramantane ($C_{22}H_{28}$), pentamantane ($C_{26}H_{32}$ and $C_{25}H_{30}$), cyclohexamantane ($C_{26}H_{30}$), super-adamantane ($C_{30}H_{36}$). Suitable diamondoids can be prepared synthetically, obtained commercially and also obtained from refinement of petroleum sources. For example, suitable diamondoid reagents for the addition of diamondoid groups to various chromophores, such as adamantyl thiol and adamantol, can be obtained commercially from suppliers such as Sigma-Aldrich. Synthetic routes for various diamondoids can also be found in the literature, for example, diamantane synthesis is described in Gund, T., et al., "Diamantane. I. Preparation of diamantane. Physical and spectral properties," J. ORG. CHEM. 39 (20):2979-2987, Oct. 1, 1974, the entire contents of which are incorporated herein by reference.

In various preferred embodiments of nonlinear optical chromophores in accordance herewith, diamondoid substituents comprise adamantyl and diamantyl groups, which may be covalently bonded to the various chromophores at the 1-position or 2-position, as represented by the following formulae:

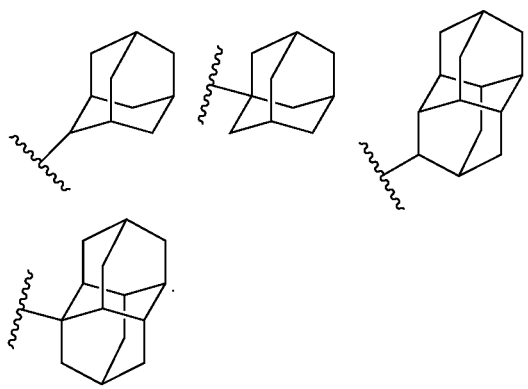

Thus, nonlinear optical chromophores in accordance herewith may include one or more such adamantyl and/or diamantyl groups covalently attached to the chromophore. Diamondoid groups may be covalently attached to chromophores in accordance with various embodiments of the present invention, for example, through ether linkages, thioether linkages, carbon-carbon bonds to aromatic moiety bearing the one or more diamondoids, and similar groups. For example, adamantyl groups can be added via nucleophilic substitution reactions of adamantyl alcohols or thiols with epoxide groups.

The present invention also includes nonlinear optical materials comprising a nonlinear optic chromophore according to an embodiment of the invention incorporated within a matrix material, as well as blends of two or more chromophores, and neat films of the chromophore alone (particularly in instances where the chromophore is amorphous). Suitable matrix materials can include polymers, such as, for example: poly(methylmethacrylate)s (PMMA); polyimides; polyamic acid; polystyrenes; poly(urethane)s (PU); and amorphous polycarbonates (APC). In various embodiments the matrix material can comprise a poly(methylmethacrylate), for example having a molecular weight of about 120,000 and a glass transition temperature Tg of about 85-165° C., or an APC having a Tg of about 150-220° C.

The nonlinear optic chromophore according to an embodiment of the invention is generally incorporated within the matrix material at a loading of 1% to 50% by weight, based on the entire nonlinear optical material, more preferably at a loading of 2% to 35% by weight, and most preferably at a loading of 3% to 35% by weight. Nonlinear optical materials in accordance with various embodiments of the invention can be in the form of solid thin films, optionally disposed on a surface of another material. In general, nonlinear optical materials according to the present invention include all existing known forms of such materials, but wherein the optical chromophore incorporated within the matrix material comprises a nonlinear optic chromophore according to an embodiment of the invention described herein.

The present invention also relates to electro-optic devices comprising a nonlinear optical material according to various embodiments of the present invention. Electro-optic device and/or system embodiments of the present invention include phased array radar, satellite and fiber telecommunications, cable television (CATV), optical gyroscopes for application in aerial and missile guidance, electronic counter measure systems (ECM) systems, backplane interconnects for high-speed computation, ultrafast analog-to-digital conversion, land mine detection, radio frequency photonics, spatial light modulation and all-optical (light-switching-light) signal processing, wherein such devices include a nonlinear optical material according to the present invention. Moreover, the extremely broad absorption spectrum of nonlinear optic chromophores according to the present invention, which essentially covers the entire UV-visible-near infrared region from 250 nm to 1800 nm at high extinction coefficient, indicates that nonlinear optical materials according to various embodiments of the present invention can also be used in solar conversion and photovoltaic devices.

One preferred electro-optic device embodiment according to the present invention includes electro-optic modulators for telecommunications, wherein the modulator comprises a nonlinear optical material according to the present invention. Another preferred device is an all-optical device. Such a device can be used for optical switching, parametric amplification and other all-optical applications of the third-order hyperpolarizability.

Various preferred chromophores in accordance with embodiments of the present invention include:

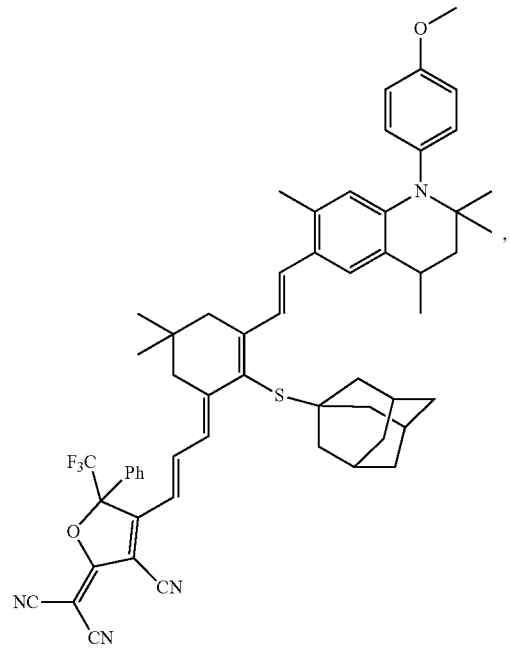

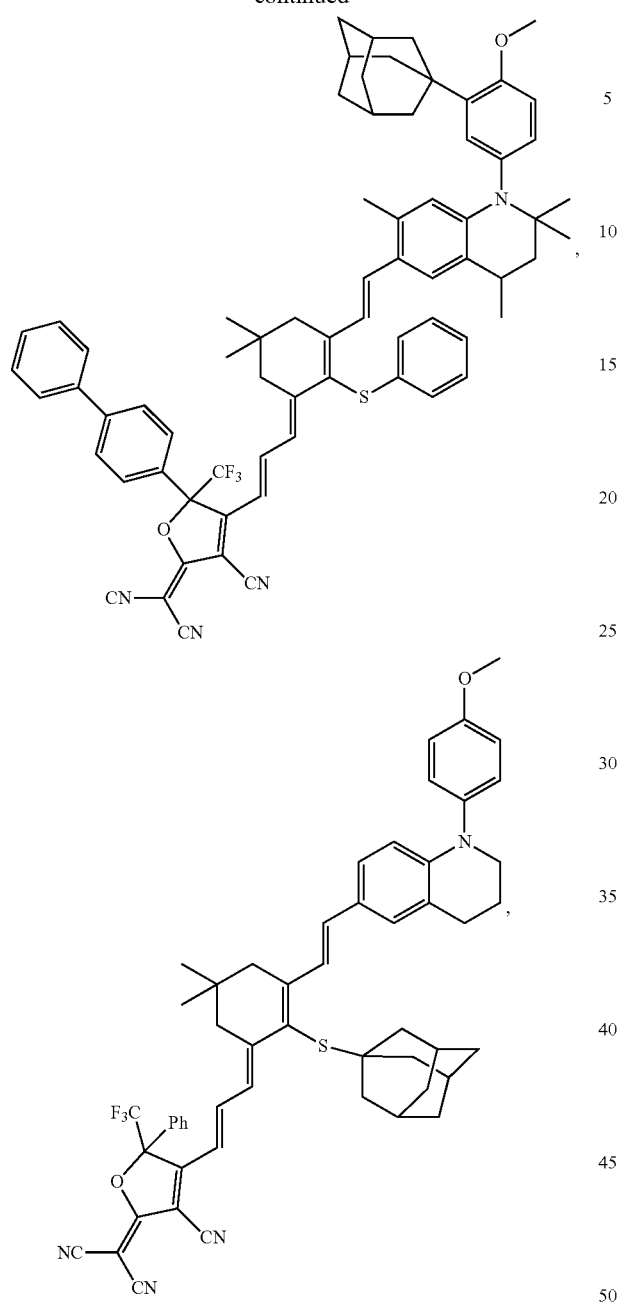
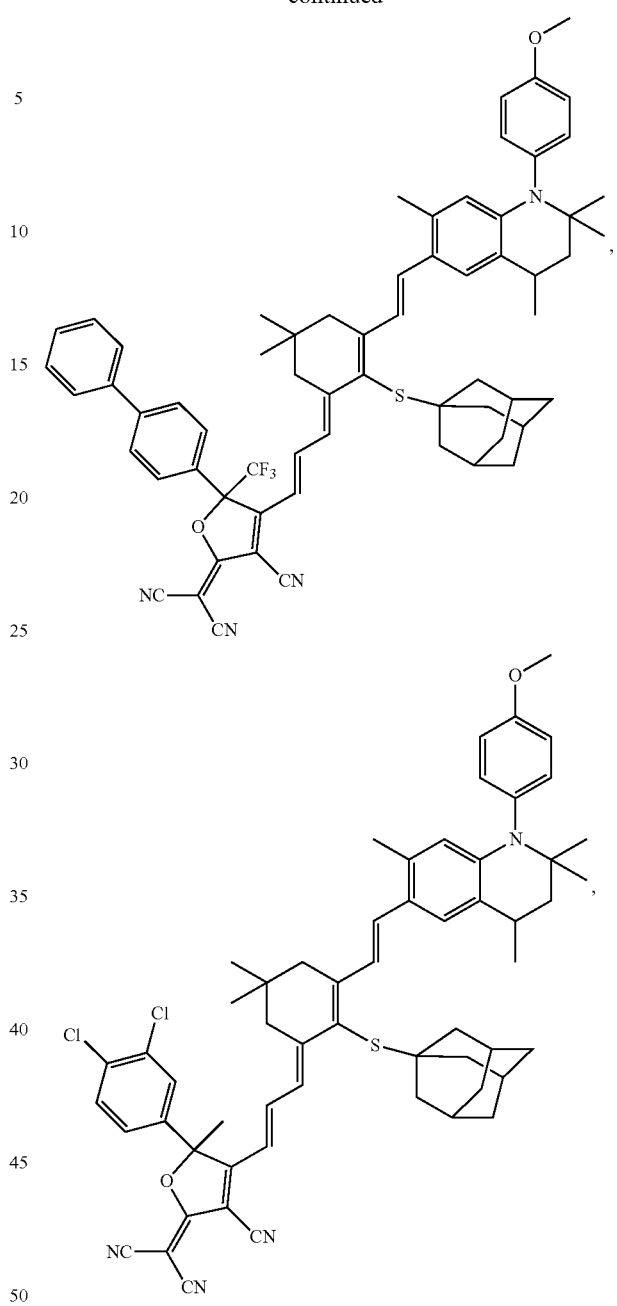

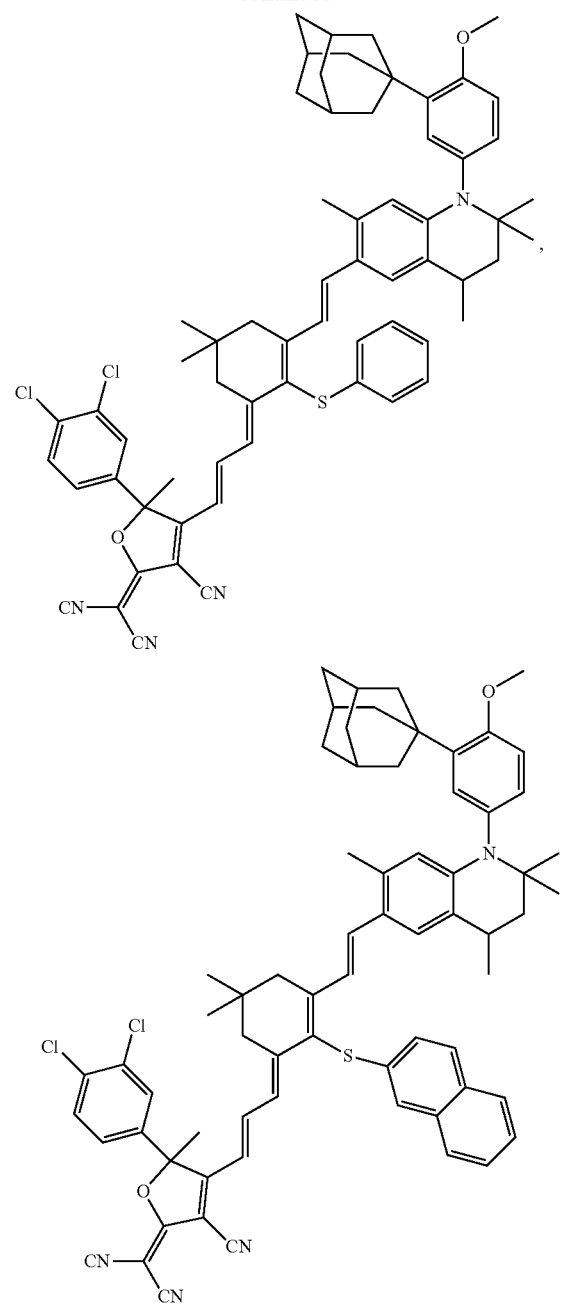
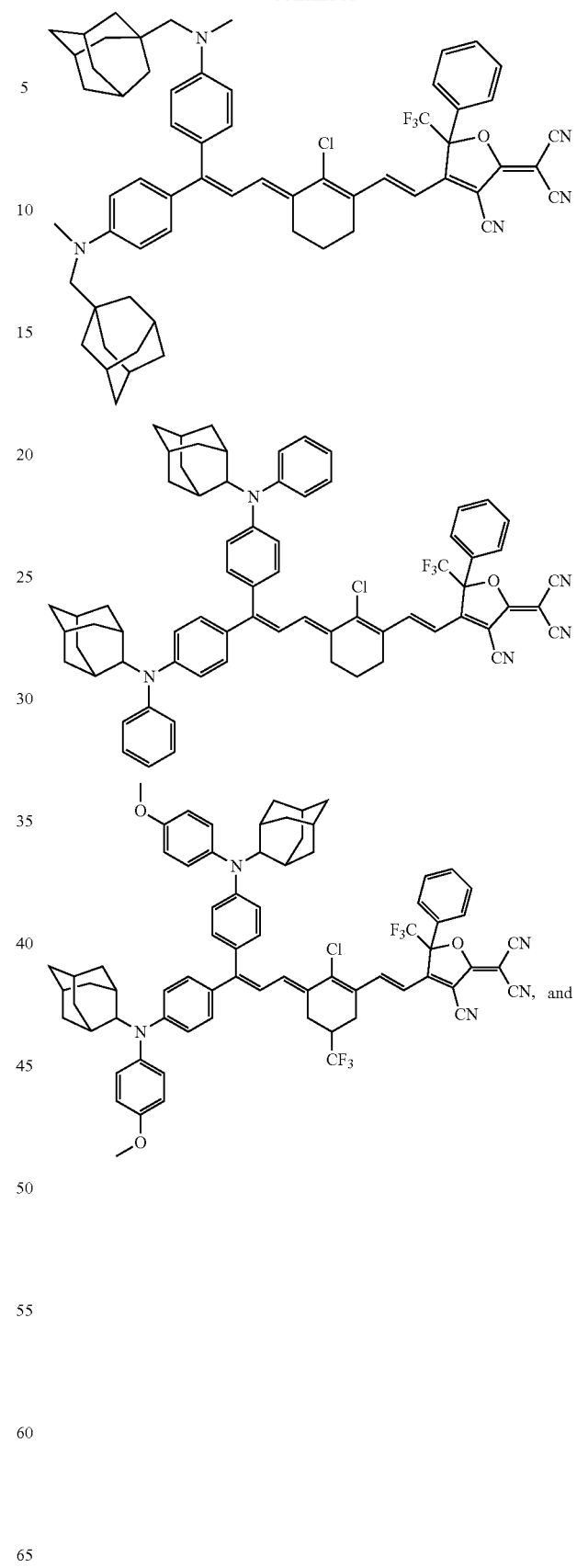

-continued

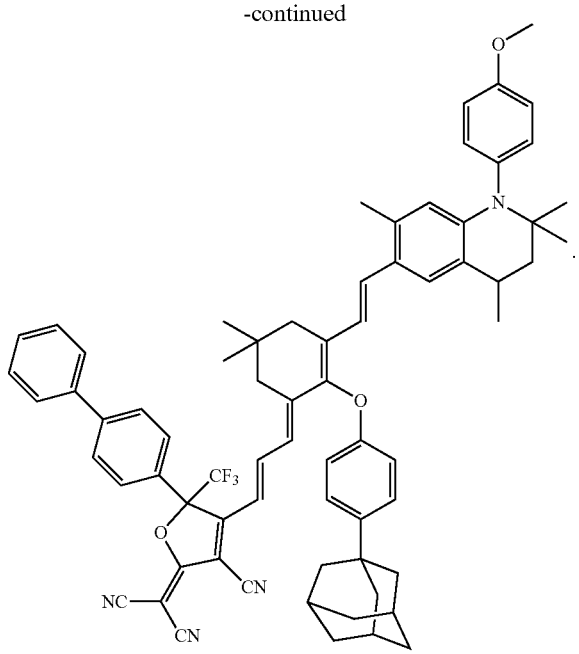

The invention will now be described in further detail with reference to the following non-limiting example.

EXAMPLES

Synthesis Example 1: Preparation of 2-[4-[(E,3 E)-3-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]prop-1-enyl]-3-cyano-5-phenyl-5-(trifluoromethyl)-2-furylidene]propanedinitrile is detailed herein Example 1a. Synthesis of 1-(4-methoxyphenyl)-2,2,4,7-tetramethyl-3,4-dihydroquinoline

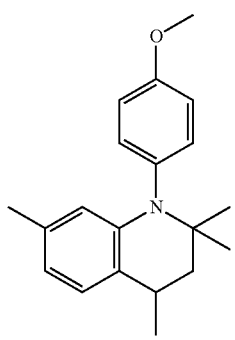

A solution of 2,2,4,7-tetramethyl-3,4-dihydro-1H-quinoline (10.0 g, 0.0528 mol) and 1-bromo-4-methoxy-benzene (83.0%, 11.9 g, 0.0528 mol) in toluene (35.0 mL) was sparged with $N_2$ then treated with potassium tert-butoxide (7.71 g, 0.0687 mol), Pd(OAc)$_2$ (0.593 g, 0.00264 mol), and tri-tert-butylphosphine (1.07 g, 0.00528 mol) The flask was fitted with a condenser, and a nitrogen line was inserted. The reaction mixture was heated to 111° C. for 64 hr.

The reaction mixture was diluted with MeOH then concentrated. The residue was taken up in dichloromethane ("DCM"), then the solids were removed by vacuum filtration. The filtrate was washed sequentially with water and brine, then the organics were dried over MgSO$_4$, filtered, and concentrated. The crude material was purified by normal-phase ("NP") chromatography (0-50% EtOAc in hexanes). The product fractions were concentrated to afford 1-(4-methoxyphenyl)-2,2,4,7-tetramethyl-3,4-dihydroquinoline (94.0%, 14.5 g, 0.0461 mol, yield: 87.3%) as an amber syrup.

Example 1b. Synthesis of 1-(4-methoxyphenyl)-2,2,4,7-tetramethyl-3,4-dihydroquinoline-6-carbaldehyde

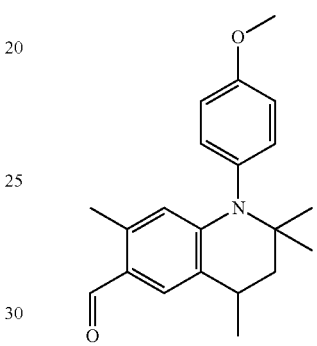

A solution of 1-(4-methoxyphenyl)-2,2,4,7-tetramethyl-3,4-dihydroquinoline (94.0%, 10.9 g, 0.0346 mol) in DMF (30.0 mL) was sparged with $N_2$ and cooled in an ice bath. POCl$_3$ (7.92 mL, 0.0865 mol) was added slowly via syringe. The mixture stirred on ice for 2 hr, at which time LCMS analysis indicated full conversion to the Vilsmeier adduct (m/z 351) and the aldehyde. The reaction was quenched by addition of water and diluted with DCM, which was stirred at room temp for 16 hr.

The reaction mixture was extracted with DCM, then the pooled organics were washed with water, dried through a phase separation paper, and concentrated. The crude material was purified by NP chromatography (0-50% EtOAc in hexanes). The product fractions were concentrated to afford 1-(4-methoxyphenyl)-2,2,4,7-tetramethyl-3,4-dihydroquinoline-6-carbaldehyde (10.6 g, 0.0326 mol, yield: 94.3%) as a pale yellow powder.

Example 1c. Synthesis of 2-(1-adamantylsulfanyl)-3,5,5-trimethyl-cyclohex-2-en-1-one

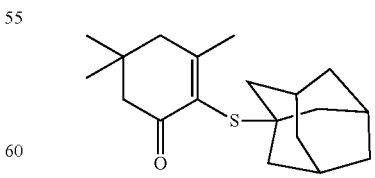

A solution of sodium ethoxide (21.0% 23.6 mL, 0.0632 mol) in ethanol (200 mL) was sparged with $N_2$ then treated with adamantane-1-thiol (95.0%, 44.8 g, 0.253 mol). The mixture was stirred at room temp under $N_2$ for 10 min, then 4,4,6-trimethyl-7-oxabicyclo[4.1.0]heptan-2-one (39.0 g, 0.253 mol) was added. The flask was capped, and the mixture continued to stir at room temperature. After 10 min, reaction mixture was quenched with water, then the solid precipitate was isolated and dried by vacuum filtration to give 2-(1-adamantylsulfanyl)-3,5,5-trimethyl-cyclohex-2-en-1-one (73.9 g, 0.243 mol, yield: 95.9%) as an off-white solid.

Example 1d. Synthesis of 2-(1-adamantylsulfanyl)-3-[(E)-2-[1-(4-methoxyphenyl)-3,4-dihydro-2H-quinolin-6-yl]vinyl]-5,5-dimethyl-cyclohex-2-en-1-one

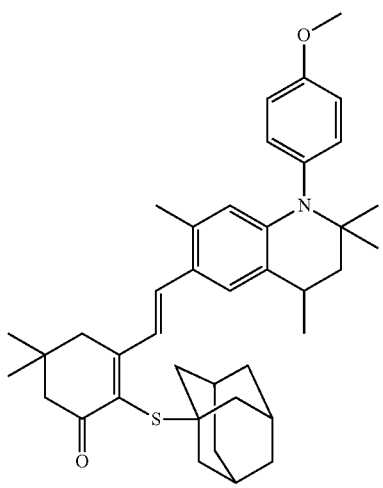

A 100 mL round-bottom flask was charged with ethanol (8.00 mL) and sparged with N₂. To this was added 1-(4-methoxyphenyl)-2,2,4,7-tetramethyl-3,4-dihydroquinoline-6-carbaldehyde (5.00 g, 0.0155 mol), 2-(1-adamantylsulfanyl)-3,5,5-trimethyl-cyclohex-2-en-1-one (4.94 g, 0.0162 mol), lithium ethoxide (95.0%, 0.212 g, 0.00386 mol), and piperidine (1.53 mL, 0.0155 mol). The flask was sealed with a septum, an N₂ line was inserted, and the mixture was stirred at 70° C. for 64 hr.

The reaction mixture was diluted with MeOH and cooled in the −20° C. freezer, then the orange solids were isolated by vacuum filtration. The material was recrystallized from 10:1 MeOH/H₂O, and the resultant solids were isolated and dried by vacuum filtration to afford 2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-one (99.0%, 7.09 g, 0.0115 mol, yield: 74.4%) as a bright orange powder.

Example 1e. Synthesis of (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetonitrile

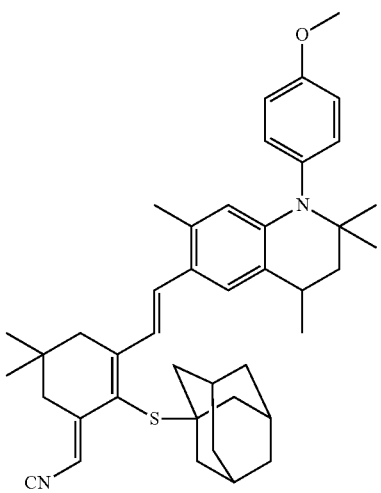

A 500 mL round bottom flask was dried with a heat gun then sparged with N₂. Then acetonitrile (3.36 mL, 0.0644 mol) in 99 mL of THF was added, and the mixture was cooled to −78° C. n-BuLi (2.50 M, 25.4 mL, 0.0636 mol) was then added dropwise over the course of ~10 min, and the mixture was allowed to stir at the same temp under N₂ for 10 min (the mixture turned opaque cloudy white). The flask was then placed in a 2-8° C. refrigerator for 30 minutes. The sealed flask was then placed back in the dry ice/acetone bath, an N₂ line was inserted, and 2-(1-adamantylsulfanyl)-3-[(E)-2-[1-(4-methoxyphenyl)-2,2,4,7-tetramethyl-3,4-dihydro-quinolin-6-yl]vinyl]-5,5-dimethyl-cyclohex-2-en-1-one (97.0%, 5.00 g, 0.00795 mol—dried under high vacuum) in an additional 54 mL of THF (sparged w/ N₂ and sonicated to ensure all solids dissolved) was added dropwise via syringe through the septum. After 3 hours, the reaction was quenched by addition of water and warmed to room temp then extracted into EtOAc. The pooled organics were dried over anhyd MgSO₄, filtered, and concentrated. The foamy orange residue was taken up in 20 mL of AcOH, then the flask was sealed with a septum, and the mixture was stirred at 70° C. for 16 hr.

The reaction mixture was diluted with DCM and washed with saturated aqueous bicarbonate. The aqueous phase was extracted with additional DCM, then the pooled organics were washed with additional saturated aqueous bicarbonate. The pooled organics were dried through a phase separation paper and concentrated. The material was eluted through a silica gel plug with DCM. The filtrate was concentrated to afford (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetonitrile (95.5%, 4.78 g, 0.00721 mol, yield: 90.7%) as a foamy red solid.

Example 1f. Synthesis of (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetaldehyde

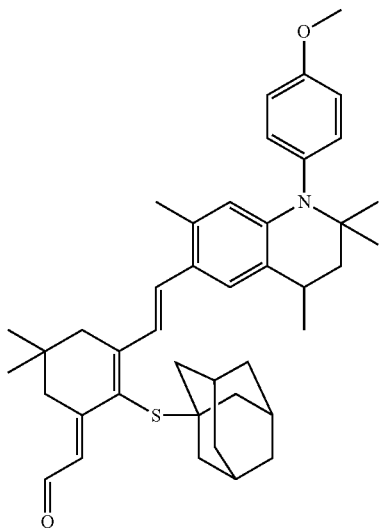

A solution of (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetonitrile (93.0%, 17.3 g, 0.0255 mol) in 55 mL of DCM was sparged with $N_2$, cooled in an ice bath, and treated with dropwise addition of diisobutyl aluminum hydride ("DIBAL") (1.00 M, 38.2 mL, 0.0382 mol). The mixture was stirred at room temp for 15 minutes.

The reaction mixture was quenched by addition of sodium sulfate decahydrate until gas evolution had ceased. The mixture was then adsorbed onto silica gel and purified by NP chromatography (100% DCM). The product fractions were concentrated to afford (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetaldehyde (10.4 g, 0.0164 mol, yield: 79.8%) as a dark red-black solid.

Example 1g. Synthesis of 2-[4-[(E,3 E)-3-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]prop-1-enyl]-3-cyano-5-phenyl-5-(trifluoromethyl)-2-furylidene]propanedinitrile

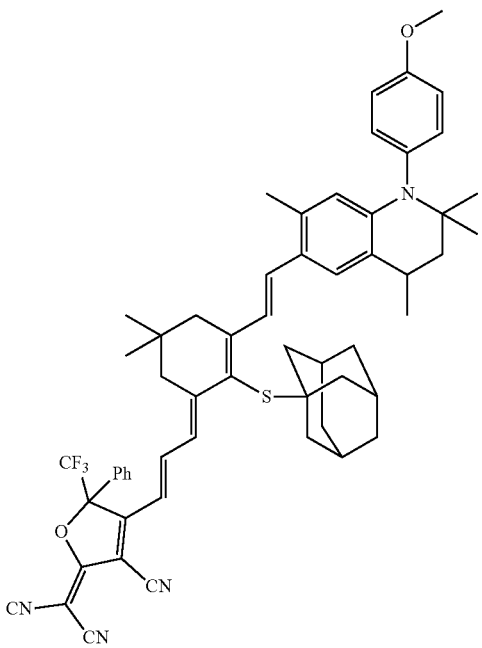

A round bottom flask containing (2 E)-2-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]acetaldehyde (96.0%, 9.52 g, 0.0144 mol) and 2-[3-cyano-4-methyl-5-phenyl-5-(trifluoromethyl)-2-furylidene]propanedinitrile (4.99 g, 0.0158 mol) was diluted with 1-propanol (50.0 mL). The mixture was sparged with $N_2$, and the flask was covered with foil to eliminate all light. The flask was sealed with a septum, an $N_2$ line was inserted, and the mixture was stirred at 66° C. for 45 min. The mixture was cooled to room temperature, and the solids were isolated by filtration. The solids were purified by NP chromatography (the prefilled cartridge was prepped by eluting 25 mL of DCM with 0.5 mL of ethylamine prior to loading the product). The product fractions were concentrated, then the residue was recrystallized from DCM/MeOH. The solids were then triturated with ethyl ether and dried to afford 2-[4-[(E,3 E)-3-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]prop-1-enyl]-3-cyano-5-phenyl-5-(trifluoromethyl)-2-furylidene]propanedinitrile (6.93 g, 0.00743 mol, yield: 51.7%) as a coppery red powder.

Liquid chromatography/mass spectroscopy (LCMS) analysis of the liquid indicated nearly full conversion to the desired product. The mixture was cooled to room temperature, and then cooled in a −20° C. freezer for 20 min. The solids were collected.

The solids were taken up in dichloromethane and filtered through a pad of silica gel, eluting with dichloromethane. Fractions 2, 3, 4 and 5 were concentrated separately and analyzed.

All four fractions were between 90 and 96% pure, so they were combined and recrystallized from a dichloromethane/methanol mixture by slow evaporation of the dichloromethane. LCMS analysis of the solids obtained from recrystallization showed ~94% purity. The solids were then soaked in diethyl ether, filtered, and dried under high vacuum to afford 2-[4-[(E,3 E)-3-[2-(1-adamantylsulfanyl)-3-[(E)-2-[1-(4-methoxyphenyl)-2,2,4,7-tetramethyl-3,4-dihydroquinolin-6-yl]vinyl]-5,5-dimethyl-cyclohex-2-en-1-ylidene]prop-1-enyl]-3-cyano-5-phenyl-5-(trifluoromethyl)-2-furylidene]propanedinitrile (0.0400 g, 4.29 e-5 mol, yield: 6.98%).

LCMS analysis: 99.6% purity. m/z 932.46, M+H $^1$H NMR (500 MHz, Solvent) δ ppm 8.22 (dd, J=40.09, 11.46 Hz, 1H) 7.71-8.10 (m, 1H) 7.61-7.70 (m, 2H) 7.51 (br s, 5H) 7.24 (br dd, J=16.04, 8.02 Hz, 1H) 7.02 (br d, J=7.45 Hz, 2H) 6.92-6.99 (m, 2H) 6.50 (dd, J=34.94, 16.04 Hz, 1H) 5.72 (s, 1H) 3.83 (s, 3H) 3.09 (br dd, J=12.03, 5.73 Hz, 1H) 2.62-2.75 (m, 1H) 2.49 (br dd, J=17.47, 4.87 Hz, 1H) 2.32-2.42 (m, 2H) 2.12 (s, 3H) 1.96 (br s, 3H) 1.89 (dd, J=13.75, 6.30 Hz, 1H) 1.84 (br s, 6H) 1.61 (br d, J=14.32 Hz, 7H) 1.43 (d, J=6.30 Hz, 3H) 1.28 (s, 3H) 1.03 (br s, 3H) 1.00 (br d, J=5.15 Hz, 3H) 0.83-0.97 (m, 3H).

Temporal Stability of Product of Synthesis Example 1: The chromophore of Synthesis Example 1 had a glass transition temperature of about 152° C. Thin films, having a thickness of 1-2 μm, prepared by dissolving the chromophore of Synthesis Example 1 (35 wt %) in 1,1,2 trichloroethane (10% solids) and spin-coating ITO coated glass substrates at 2000 rpm were prepared. The solvent was removed under vacuum at 80° C. for 16 hrs. Gold pads (50 nm) were sputtered on the film to create the top electrode. These simple devices were then poled at 155° C. and 100 V/μm under nitrogen for 60 s and cooled with the field on to preserve the poled state. Initial measurements of the electro-optic coefficient (r33) were made, and the samples were stored in an oven at 85° C. and re-measured periodically. The results are set forth below in Table 1 and are depicted graphically in FIG. 1. As can be seen from the data in Table 1 and FIG. 1, the electro-optical performance of thin films prepared using a chromophore according to an embodiment of the present invention exhibit significant, long-term thermal stability.

TABLE 1

Temporal Stability of Synthesis Example 1 Thin Films
($r_{33}$ remaining after storage at 85° C.)

| Time (Hours) | $r_{33}$ Remaining (%) |
|---|---|
| 0 | 100 |
| 64 | 91.4 |
| 398 | 90.8 |
| 704 | 89.8 |

Synthesis Example 2: Preparation of 2-[4-[(E,3 E)-3-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]prop-1-enyl]-3-cyano-5-(4-phenylphenyl)-5-(trifluoromethyl)-2-furylidene]propanedinitrile is detailed herein Example 2a. Synthesis of 1-[3-(1-adamantyl)-4-methoxy-phenyl]-2,2,4,7-tetramethyl-3,4-dihydroquinoline

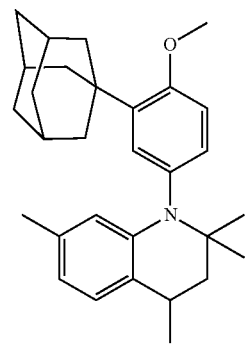 [SMILES: COc1ccc(N2c3cc(C)ccc3C(C)CC2(C)C)cc1C12CC3CC(CC(C3)C1)C2]

A solution of 2,2,4,7-tetramethyl-3,4-dihydro-1H-quinoline (24.5 g, 0.129 mol) and 1-(5-bromo-2-methoxy-phenyl)adamantane (97.0%, 50.0 g, 0.151 mol) in 70 mL of toluene was sparged with $N_2$ then treated with sodium tert-butoxide (16.2 g, 0.168 mol), Pd(OAc)$_2$ (1.45 g, 0.00647 mol), and tri-tert-butylphosphine (2.62 g, 0.0129 mol). The flask was fitted with a condenser, and a nitrogen line was inserted. The reaction mixture was heated to 111° C. for 60 hr.

The reaction mixture was diluted with DCM, then the solids were removed by vacuum filtration. The filtrate was purified by NP chromatography (50% DCM in hexanes—isocratic eluent). The product fractions were concentrated to give a highly impure product. The solids were dissolved in 500 mL of DCM which sat at room temperature for 16 hr. The DCM volume was reduced to ~200 mL, then methanol was added. The mixture was stirred until solids began to form. Tan solids precipitated out of the mixture. These solids were isolated and dried by vacuum filtration to give the product in 87% purity. The solids were then soaked in methanol for 1 hr at room temperature then re-isolated and dried to afford 1-[3-(1-adamantyl)-4-methoxy-phenyl]-2,2,4,7-tetramethyl-3,4-dihydroquinoline (92.0%, 39.8 g, 0.0852 mol, yield: 65.8%) as a yellowish-tan solid.

Example 2b. Synthesis of 1-[3-(1-adamantyl)-4-methoxy-phenyl]-2,2,4,7-tetramethyl-3,4-dihydroquinoline-6-carbaldehyde

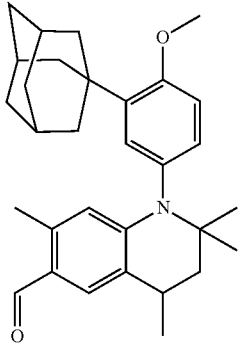 [SMILES: COc1ccc(N2c3cc(C)c(C=O)cc3C(C)CC2(C)C)cc1C12CC3CC(CC(C3)C1)C2]

A solution of N,N-dimethylformamide (18.0 mL, 0.232 mol) in dichloromethane (50 mL) was sparged with $N_2$ and cooled on ice. Then $POCl_3$ (9.35 mL, 0.102 mol) was added, and the mixture was stirred at the same temp for ~30 min, until the solution turned a pale pink color. Then 1-[3-(1-adamantyl)-4-methoxy-phenyl]-2,2,4,7-tetramethyl-3,4-dihydroquinoline (92.0%, 21.7 g, 0.0464 mol), in an additional 50 mL of DCM, was added slowly. The mixture was stirred 20 min then quenched by slow addition of 10% aqueous $Na_2CO_3$, and this was stirred vigorously for 16 hr.

The aqueous and organic layers were separated, then the aqueous was extracted with additional DCM. The pooled organics were dried through a phase separation paper and purified by NP chromatography (0-50% ethyl acetate in hexanes). The product fractions were concentrated to afford 1-[3-(1-adamantyl)-4-methoxy-phenyl]-2,2,4,7-tetramethyl-3,4-dihydroquinoline-6-carbaldehyde (97.5%, 15.3 g, 0.0326 mol, yield: 70.2%) as a pale yellow solid.

Example 2c. Synthesis of 3,5,5-trimethyl-2-phenylsulfanyl-cyclohex-2-en-1-one

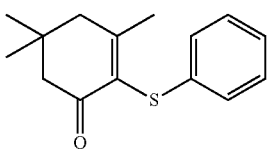 [SMILES: CC1=C(Sc2ccccc2)C(=O)CC(C)(C)C1]

A solution of benzenethiol (10.1 mL, 0.106 mol) in ethanol (75.0 mL) was treated with sodium ethoxide (21.0%, 7.50 mL, 0.0201 mol). The mixture was stirred at room temperature for 20 min, then 4,4,6-trimethyl-7-oxabicyclo[4.1.0]heptan-2-one (15.5 g, 0.101 mol) was added dropwise over the course of ~20 min. Halfway through the addition, the reaction flask was placed on ice to try to mitigate the exotherm. LCMS analysis immediately after full addition of isophorone indicated full conversion to desired product.

The reaction mixture was diluted with DCM and concentrated. The residue was then purified by NP chromatography (0-50% ethyl acetate in hexanes). The appropriate fractions were concentrated to afford 3,5,5-trimethyl-2-phenylsulfanyl-cyclohex-2-en-1-one (92.6%, 24.5 g, 0.0923 mol, yield: 91.8%) as a yellow syrup that quickly solidified as it cooled.

Example 2d. Synthesis of 3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-one

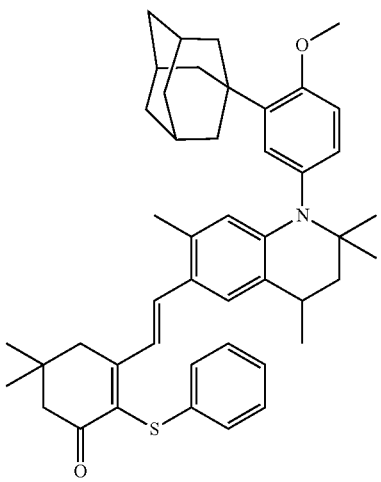

A mixture of 1-[3-(1-adamantyl)-4-methoxy-phenyl]-2,2,4,7-tetramethyl-3,4-dihydroquinoline-6-carbaldehyde (97.5%, 15.3 g, 0.0326 mol) in ethanol (25.0 mL) was sparged with $N_2$. To this was added 3,5,5-trimethyl-2-phenylsulfanyl-cyclohex-2-en-1-one (10.4 g, 0.0423 mol), lithium ethoxide (95.0%, 0.446 g, 0.00815 mol), and piperidine (3.22 mL, 0.0326 mol). The flask was sealed with a septum, and the mixture was stirred at 70° C. for 60 hr.

The mixture was cooled to room temperature then diluted with 50% $MeOH/H_2O$ and cooled in 2-8° C. refrigerator. Some red solids were isolated by vacuum filtration. The material was recrystallized from 50% $MeOH/H_2O$, and the resultant solids were isolated and dried by vacuum filtration. The solids were then adsorbed onto silica gel and purified by NP chromatography (100% DCM). The appropriate fractions were concentrated to afford 3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-one (81.0%, 23.9 g, 0.0282 mol, yield: 86.6%) as bright red-orange flakes.

Example 2e. Synthesis of (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene] acetonitrile

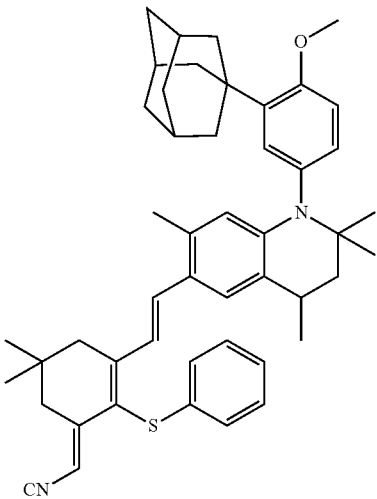

A solution of sodium hydride (60.0%, 4.06 g, 0.102 mol) in THF (100 mL) was sparged with $N_2$ at room temperature. Diethyl cyanomethylphosphonate (98.0%, 16.8 mL, 0.102 mol) was then added dropwise (with significant gas evolution), and the mixture was stirred under $N_2$ atmosphere at room temperature until it became transparent (~20 min). 3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-one (81.0%, 21.5 g, 0.0254 mol), in an additional 50 mL of THF, was added, the flask was fitted with a condenser, and the mixture was stirred at reflux 16 hours.

The reaction mixture was concentrated, then the residue was purified by NP chromatography (50-100% DCM in hexanes). The appropriate fractions were concentrated to afford the product with only 77% purity. The material was taken up in a minimal volume of DCM. To this was added MeOH. A gentle $N_2$ stream was applied to the solution to facilitate evaporation of DCM. At first, the product seemed to come out of solution as a dark viscous mass. Then as more DCM evaporated, a bright orange solid precipitated out. After ~15-20 minutes, the solids were isolated and dried by vacuum filtration to afford (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]acetonitrile (93.0%, 15.8 g, 0.0207 mol, yield: 81.6%) as a bright orange solid.

Example 2f. Synthesis of (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene] acetaldehyde

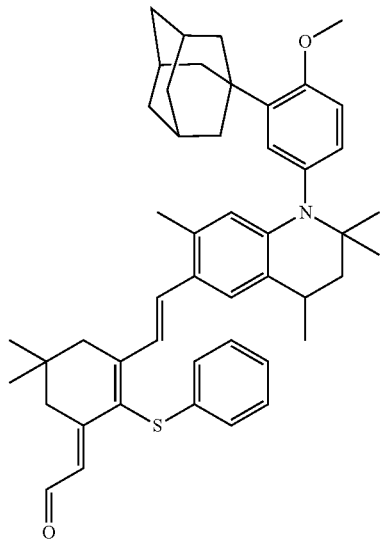

A solution of (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]acetonitrile (93.0%, 15.8 g, 0.0207 mol) in 50.0 mL of DCM was sparged with $N_2$ and treated with dropwise addition of DIBAL (1.00 M, 22.8 mL, 0.0228 mol). The mixture was stirred at room temperature—after 15 minutes, LCMS indicated only ~26% conversion of starting material to the imine and aldehyde. An additional 15 mL of DIBAL was added, and the mixture stirred 16 hr.

The reaction mixture was then quenched by addition of sodium sulfate decahydrate until gas evolution had ceased. The mixture was then adsorbed onto silica gel and purified by NP chromatography (75-100% DCM in hexanes). The product fractions were concentrated, and LCMS analysis indicated full hydrolysis to the aldehyde with ~95% purity. The solids were then recrystallized from DCM/MeOH to afford (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]acetaldehyde (95.0%, 12.7 g, 0.0169 mol, yield: 81.5%) as a deep red solid.

Example 2f. Synthesis of 2-[4-[(E,3 E)-3-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]prop-1-enyl]-3-cyano-5-(4-phenylphenyl)-5-(trifluoromethyl)-2-furylidene]propanedinitrile

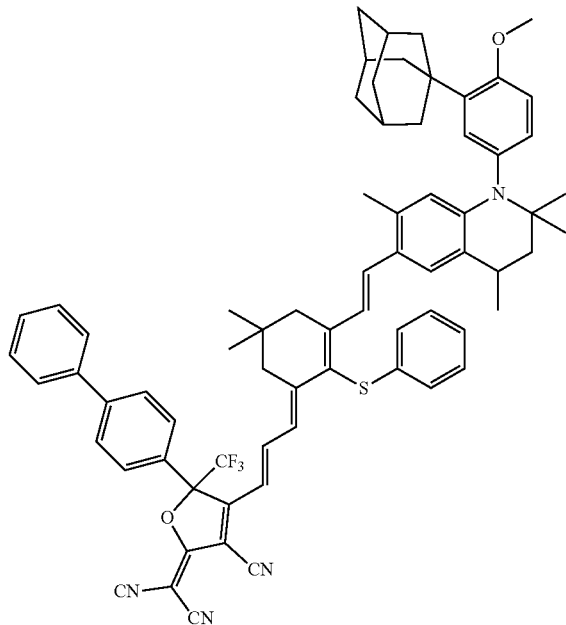

A round bottom flask containing (2 E)-2-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]acetaldehyde (95.0%, 12.7 g, 0.0169 mol) and 2-[3-cyano-4-methyl-5-(4-phenylphenyl)-5-(trifluoromethyl)-2-furylidene]propanedinitrile (7.27 g, 0.0186 mol) was diluted with 1-propanol (40.0 mL). The mixture was sparged with $N_2$, and the flask was covered with foil to eliminate all light. The flask was sealed with a septum, an $N_2$ line inserted, and the mixture was stirred at 65° C. for 24 hr. An additional 0.1 eq of acceptor was added to the mixture, then the mixture was cooled to room temperature, and the mixture stirred at this temperature for 60 hr. The heat was then increased to 70° C., an additional 0.1 eq of acceptor was added, and the mixture stirred 1.5 hr. The mixture was cooled to room temperature, then further cooled in a 2-8° C. refrigerator.

The solids were then isolated by filtration. The solids were collected and dissolved in DCM. About half of the material was used to test purification conditions. Three ground-glass fritted funnels were prepared with slurries of different chromatography media: neutral $Al_2O_3$, basic $Al_2O_3$, and $SiO_2$ (prepared with ~1 mL of NEt3). About ⅓ of the DCM solution that was set aside for testing was eluted through each of the three media. After full elution, TLC and LCMS analyses were performed. It appeared that $SiO_2$ was superior in removing baseline material. The eluted material was combined and concentrated. The material was dissolved in a minimal amount of DCM (to make a thick syrup), then MeOH was added. The mixture was cooled in the refrigerator for 1 hr, then the solids were collected by vacuum filtration. This procedure was performed five more times until that portion had attained >99% purity. The remaining half of the original material was split into two more portions, and the same purification procedures were performed.

The solids from all batches were combined and collected by vacuum filtration to afford 2-[4-[(E,3 E)-3-[3-[(E)-2-[1-[3-(1-adamantyl)-4-methoxy-phenyl]-2,2,4,7-tetramethyl-3,4-dihydroquinolin-6-yl]vinyl]-5,5-dimethyl-2-phenylsulfanyl-cyclohex-2-en-1-ylidene]prop-1-enyl]-3-cyano-5-(4-phenylphenyl)-5-(trifluoromethyl)-2-furylidene]propanedinitrile (7.68 g, 0.00708 mol, yield: 41.9%) as a black powder.

$^1$H NMR (500 MHz, ACETONE-$d_6$) δ ppm 7.98-8.12 (m, 1H) 7.84-7.93 (m, 3H) 7.79 (d, J=8.59 Hz, 2H) 7.71 (d, J=7.45 Hz, 2H) 7.54 (d, J=12.03 Hz, 1H) 7.38-7.51 (m, 4H) 7.20-7.25 (m, 2H) 7.15-7.19 (m, 2H) 7.06-7.11 (m, 1H) 7.02-7.06 (m, 1H) 6.87-6.98 (m, 2H) 6.69 (br d, J=14.32 Hz, 1H) 5.67 (s, 1H) 3.89 (d, J=2.86 Hz, 3H) 2.92-3.06 (m, 1H) 2.79 (br s, 4H) 2.75 (s, 2H) 2.48-2.60 (m, 1H) 2.38-2.47 (m, 1H) 2.03-2.12 (m, 9H) 1.91 (dd, J=13.17, 5.15 Hz, 1H) 1.74 (br d, J=8.02 Hz, 6H) 1.63 (q, J=13.17 Hz, 1H) 1.17-1.34 (m, 6H) 0.96-1.15 (m, 6H) 0.88-0.94 (m, 3H).

Figure 2:
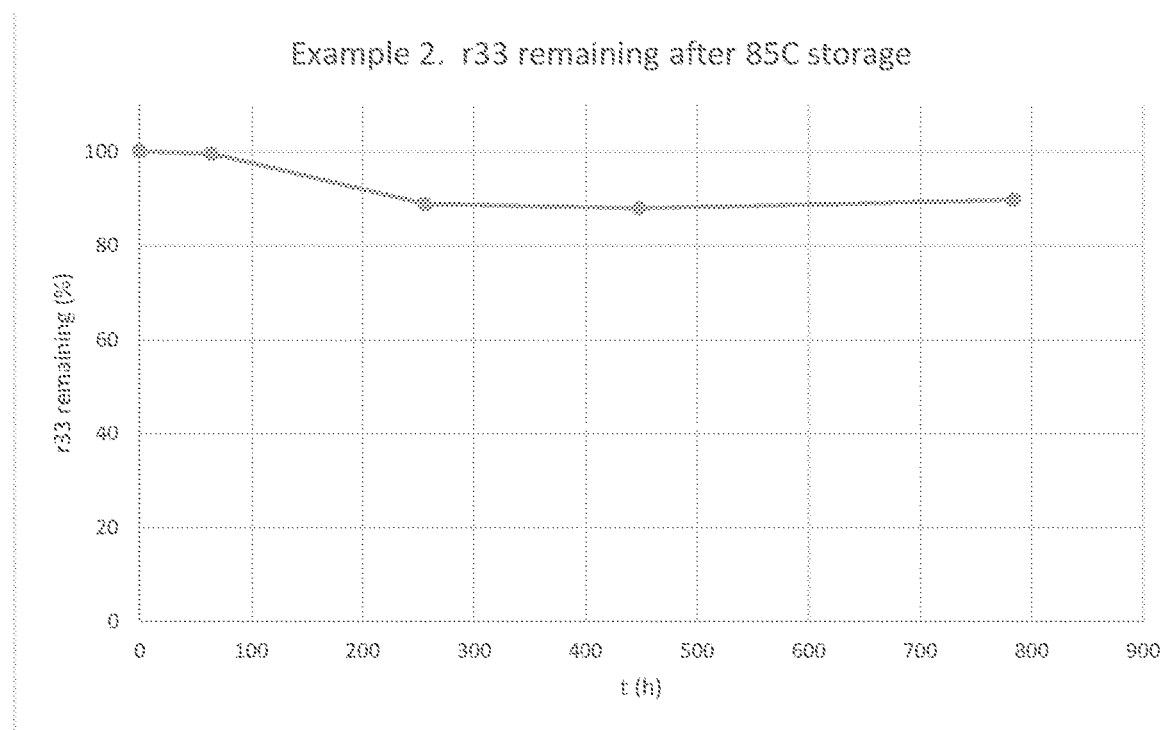
FIG. 2 is a graphical depiction of the temporal thermal stability of a thin film coating prepared using the chromophore of Synthesis Example 2.

Temporal Stability of Product of Synthesis Example 2: The chromophore of Synthesis Example 2 had a glass transition temperature of about 176° C. Thin films, having a thickness of 1-2 m, prepared by dissolving the chromophore of Synthesis Example 2 (35 wt %) in 1,1,2 trichloroethane (10% solids) and spin-coating ITO coated glass substrates at 2000 rpm were prepared. The solvent was removed under vacuum at 80° C. for 16 hrs. Gold pads (50 nm) were sputtered on the film to create the top electrode. These simple devices were then poled at 155° C. and 100 V/μm under nitrogen for 60 s and cooled with the field on to preserve the poled state. Initial measurements of the electro-optic coefficient (r33) were made, and the samples were stored in an oven at 85° C. and re-measured periodically. The results are set forth below in Table 2 and are depicted graphically in FIG. 2. As can be seen from the data in Table 2 and FIG. 2, the electro-optical performance of thin films prepared using a chromophore according to an embodiment of the present invention exhibit significant, long-term thermal stability.

TABLE 2

Temporal Stability of Synthesis Example 2 Thin Films
($r_{33}$ remaining after storage at 85° C.)

| Time (Hours) | $r_{33}$ Remaining (%) |
|---|---|
| 0 | 100 |
| 64 | 99.6 |
| 256 | 88.9 |
| 448 | 87.9 |
| 784 | 89.7 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims

What is claimed is:

1. An electro-optical film comprising a nonlinear optical chromophore dispersed and poled within a host polymer matrix, wherein the nonlinear optical chromophore of the general formula (I):

D-π-A     (I)

wherein D represents an organic electron-donating group;
A represents an organic electron-accepting group having an electron affinity greater than the electron affinity of D; and π represents a π-bridge between the organic electron-accepting group and the organic electron-donating group; wherein the π-bridge between the organic electron-accepting group and the organic electron-donating group has the following formula ($\pi°$):

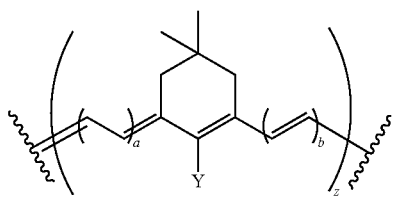

(II$^d$)

wherein each Y independently represents a sulfur linked aryl group of the following formula ($\pi^1$)

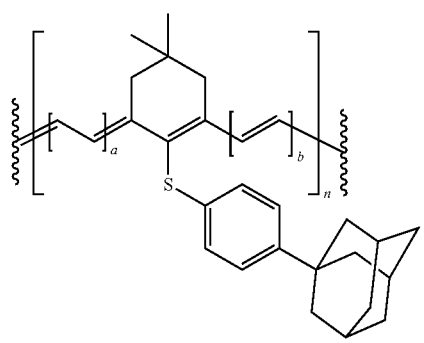

(II$^1$)

wherein each a and b independently represents an integer of 0 to 3; and z represents an integer of 1 to 3;
the nonlinear optical chromophore comprising one or more diamondoids, wherein each of the one or more diamondoids is covalently bound to one of the organic electron-accepting group, or the organic electron-donating group.

2. An electro-optical film comprising a nonlinear optical chromophore dispersed and poled within a host polymer matrix, wherein the nonlinear optical chromophore of the general formula (I):

D-π-A    (I)

wherein D represents an organic electron-donating group;
A represents an organic electron-accepting group having an electron affinity greater than the electron affinity of D; and π represents a π-bridge between the organic electron-accepting group and the organic electron-donating group; wherein the π-bridge between the organic electron-accepting group and the organic electron-donating group has the following formula ($\pi°$):

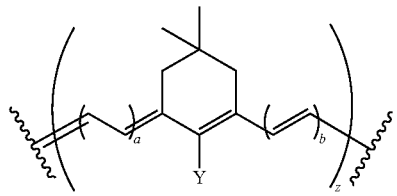

(II$^d$)

wherein each Y independently represents a sulfur linked aryl group of the following formula ($\pi^2$)

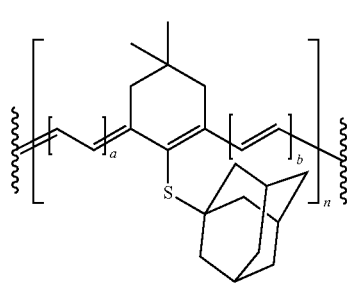

(II$^2$)

wherein each a and b independently represents an integer of 0 to 3; and z represents an integer of 1 to 3;
the nonlinear optical chromophore comprising one or more diamondoids, wherein each of the one or more diamondoids is covalently bound to one of the organic electron-accepting group, or the organic electron-donating group.

3. An electro-optical film comprising a nonlinear optical chromophore dispersed and poled within a host polymer matrix, wherein the nonlinear optical chromophore of the general formula (I):

D-Π-A    (I)

wherein D represents an organic electron-donating group;
A represents an organic electron-accepting group having an electron affinity greater than the electron affinity of D; and Π represents a Π-bridge between the organic electron-accepting group and the organic electron-donating group; wherein the Π-bridge has the following formula (II$^d$):

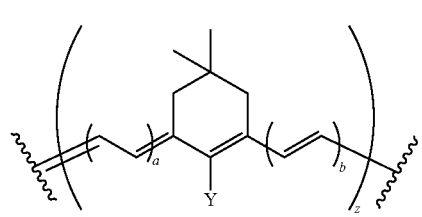

(II$^d$)

wherein Y represents a phenylsulfanyl; wherein each a and b independently represents an integer of 0 to 3; and z represents an integer of 1 to 3;
the nonlinear optical chromophore comprising a diamondoid covalently bound to the organic electron-donating group.

4. The electro-optical film according to claim 3, wherein the organic electron-accepting group has the general formula (I$^a$):

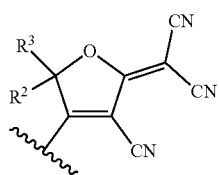
(I$^a$)

wherein R$^2$ and R$^3$ each independently represents a moiety selected from the group consisting of H, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, and (CH$_2$)$_n$—O—(CH$_2$)$_n$ where n is 1-10.

5. The electro-optical film according to claim 3, wherein the diamondoid is an adamantyl group.

* * * * *